United States Patent
Li et al.

(10) Patent No.: US 11,850,117 B2
(45) Date of Patent: Dec. 26, 2023

(54) CONFIGURABLE BREATHING ASSIST MOUTHPIECE DEVICE

(71) Applicant: GOLDEN GALAXY CORPORATION, Henderson, NV (US)

(72) Inventors: Matthew Siyuan Li, Palmetto Bay, FL (US); Bolin Miao, Shaanxi (CN); Tian Luan, Miami Lakes, FL (US); Irina Olisha Chiang, Great Neck, NY (US); Sophie Sunny Wang, Jericho, NY (US); Ivan Oliver Chiang, Great Neck, NY (US)

( * ) Notice: Subject to any disclaimer, the term of this patent is extended or adjusted under 35 U.S.C. 154(b) by 0 days.

(21) Appl. No.: 18/449,539

(22) Filed: Aug. 14, 2023

(65) Prior Publication Data

US 2023/0381011 A1 Nov. 30, 2023

(51) Int. Cl.
*A61F 5/56* (2006.01)
*A61F 5/05* (2006.01)

(52) U.S. Cl.
CPC .................................. *A61F 5/05* (2013.01)

(58) Field of Classification Search
CPC ... A61C 7/36; A61F 5/56; A61F 5/566; A61F 2005/563; A63B 71/085; A63B 2071/086; A63B 2071/088
See application file for complete search history.

(56) References Cited

U.S. PATENT DOCUMENTS

| 4,457,708 | A | * | 7/1984 | Dufour | A61C 7/00 |
|---|---|---|---|---|---|
| | | | | | 433/6 |
| 6,371,758 | B1 | * | 4/2002 | Kittelsen | A63B 71/085 |
| | | | | | 128/861 |
| 9,585,732 | B2 | * | 3/2017 | Piancino | A61F 5/566 |
| 2009/0159089 | A1 | * | 6/2009 | Jansheski | A61F 5/566 |
| | | | | | 128/861 |

OTHER PUBLICATIONS

Takai et al., "Maximum Bite Force Analysis in Different Age Groups," International Archives of Otorhinolaryngology vol. 18 No. 3/2014.
Brunton et al., "Estimation of jaw-opening forces in adults," Orthod, Craniofac. Res. 2017;1-6.

* cited by examiner

*Primary Examiner* — Camtu T Nguyen
(74) *Attorney, Agent, or Firm* — Stephen E. Zweig

(57) ABSTRACT

A mouthpiece device and method for helping human users with congested sinuses breathe freely through their mouths while sleeping while minimizing the risks of dry mouth and drooling. The device fits between the user's jaws and is configured to apply a gentle jaw and lip opening pressure sufficient to at least partially open a sleeping user's jaw and lips while the jaw and lip muscles are relaxed. At the same time, the device is configured to so that when the user, while still sleeping, activates their jaw or lip muscles to swallow, this action overcomes the gentle opening force, allowing the user to easily swallow without conscious effort. Methods of configuring the device shape and opening forces are also taught.

19 Claims, 6 Drawing Sheets

CONFIGURABLE BREATHING ASSIST MOUTHPIECE DEVICE

BACKGROUND OF THE INVENTION

Field of the Invention

This invention is in the field of mouthpiece devices to help individuals suffering from clogged sinuses to breathe by mouth during sleep.

Description of the Related Art

Nighttime breathing appliances, such as CPAP devices, anti-snore devices and similar devices are commonly used to help individuals suffering from snoring, sleep apnea, and other breathing disorders breathe comfortably during their sleep.

Other types of mouth devices include various mouth inserts to help prevent teeth grinding during sleep. Still, other types of mouth devices, such as braces, can be used to slowly reposition the alignment of the user's teeth.

However, as allergy sufferers can attest, another type of sleep-breathing problem occurs when the individual's sinuses become blocked by inflammation or other cause. Nose breathing now becomes impossible, making breathing by mouth the only option. However, if the individual's mouth remains continually open, their mouth will dry out, and/or they will have trouble managing their saliva during sleep. This leads to difficulties in sleeping and excessive drying of the mouth tissues.

Prior art studies on the maximum amount of force exerted by human jaws at different ages include the work of Takai et al., International Archives of Otorhinolaryngology Vol. 18 No. 3/2014. Prior art studies on the minimum amount of force required to open human jaws include the work of Brunton et al., Orthod, Craniofac. Res. 2017;1-6.

BRIEF SUMMARY OF THE INVENTION

The invention was inspired, in part, by the insight that what is needed is a new type of mouth device that operates to assist breathing while the user is asleep. This new type of device should fit between the user's jaws and apply a gentle jaw and lip opening pressure sufficient to at least partially open the user's jaw and lips when the user's jaw muscles and lip muscles are relaxed. At the same time, the pressure exerted by the device should be precisely calibrated so that when the still-sleeping user activates their jaw and lip muscles to swallow saliva, the device yields, allowing the user to close their jaws and lips without exerting conscious effort.

Such a device needs to adjust to the dimensions of an individual user's mouth and have a jaw and lip opening force adjusted to be just above the minimum opening force for that particular user. Here, we disclose both such an adjustable device and a method for adjusting the device to apply suitable jaw and opening force for a given user.

DETAILED DESCRIPTION OF THE INVENTION

Figure 1:
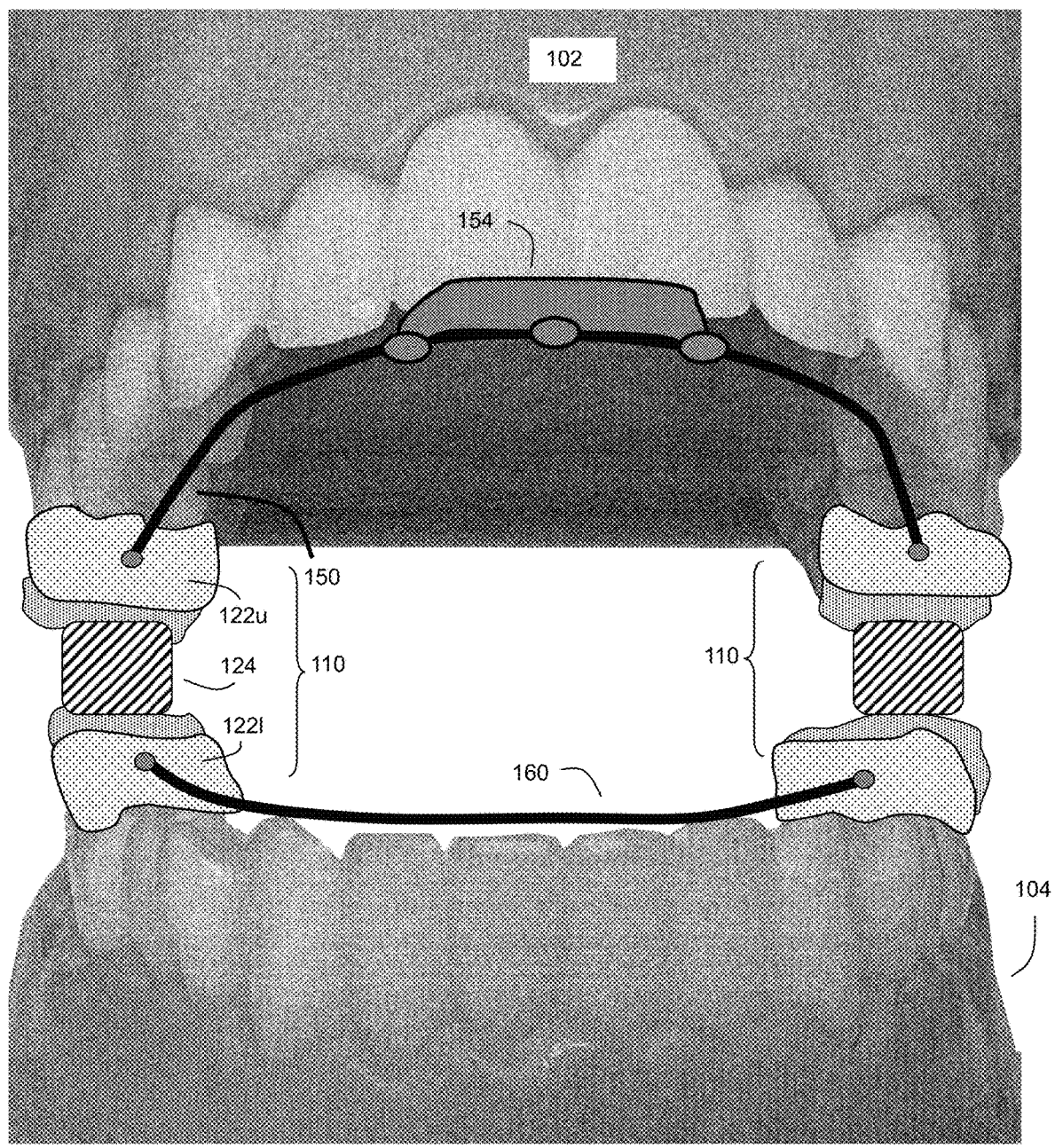
FIG. 1 shows an overview of how the mouthpiece device fits between a human user's upper and lower jaws.

FIG. 1 shows an overview of how the mouthpiece device (see FIG. 2 100) fits between the upper (102) and lower jaws (104) of a human user. This device typically comprises at least two pivoting dental blocks (110) that fit on opposite sides of the user's jaw. These pivoting dental blocks are connected to each other by an upper (150) and lower (160) archwire. Each pivoting dental block has an upper and lower wire interface face (122u, 122l), and is configured to accept an archwire end (151). The upper archwire (150) also has a lip-opening fixture (154). Here the pivots (124) are spring pivots configured to both pivot and apply an opening force to the dental block.

Put alternatively, in some embodiments, the invention may be a method of using an adjustable mouthpiece device (100) to facilitate the breathing of a human user during sleep, as well as the device (100) itself. The method typically comprises adjusting this adjustable mouthpiece device (100) to fit at least some of the mouth, jaw, teeth, and lips of this human user. The adjustable mouthpiece device (100) itself is relatively complex, and can comprise various components described below.

The device typically comprises at least two pivoting dental blocks (110). Each of these pivoting dental blocks are configured to fit inside opposite sides of the user's jaws (102, 104), usually in the back of the jaw over the user's rear molars. The dental blocks may often be a composite of different materials, with the overall structure formed from materials such as polyethylene-polyvinylacetate copolymer (EVA), silicone, or acrylic resin, or other lightweight, hypoallergenic materials. These may be supplemented by other materials, including metals or alternative plastics for pivots, springs, and screws, and softer deformable plastics for sections of the dental blocks that come into contact with the user's teeth.

These pivoting dental blocks (110) are connected by an upper (150) and lower (160) archwire. Each archwire comprises two wire ends (see FIG. 2, 151), and is generally curved in a "U" shaped structure, roughly following the contours of the patient's dental arch, where each archwire has about 170-190 degrees of curvature so that both wire ends fit inside of the user's mouth. Here common dental or orthodontic archwire materials, which are often made from stainless steel, nickel Titanium, and Beta Titanium may be used. The archwire material and thickness may be chosen to optimize certain spring-force aspects of the invention, as will be discussed shortly.

Each pivoting dental block (110) will typically comprise gap-separated upper (122u) and lower wire (122l) interface faces, as well as gap-separated upper and lower fastener faces (see FIG. 2, 130u), upper and lower tooth-accepting faces (see FIG. 3 132u, 132l), and at least some other faces.

Each gap-separated upper and lower wire interface faces (122u, 122l) will typically comprise a wire hole (FIG. 2, 124) configured to admit one of the archwire wire ends (151). Thus, when these wire ends (151) are inserted into the wire holes (124), and fastened (often with a screw, although adhesive may be used) to the upper and lower wire interface faces (122u, 122l), the upper archwire (150) connects the upper wire interface faces (122u) of the two pivoting dental blocks. Similarly, the lower archwire (160) connects the lower wire interface faces (122l) of the two pivoting dental blocks (110).

To apply gentle force to open the user's lips, at least the upper archwire (150) may be further configured with a lip opening fixture (154). This is usually positioned midway between the upper archwire's wire ends (151). The lip opening fixture is configured to extend outside of the user's jaw and past at least a middle portion of the user's upper lip (see FIG. 4, 170u). Usually this will only extend a fraction of an inch, such as ¼ to ½ inch past the lip, to apply an elevation force to partially elevate the user's lip (170u) enough above its normal resting state to allow air to enter and exit. Here, the lip opening fixture and archwire can be selected to be partially bendable so that the user can adjust them for optimal comfort and performance.

In a preferred embodiment, the upper and lower tooth-accepting faces (132u, 132) further comprise recesses configured to accommodate at least some of said teeth. The tooth-accepting faces need not be made from the same material as the bulk of the pivoting dental block, but instead may be made from alternate materials. These alternate materials can include thermoplastic materials that deform upon application of heat, but then harden, so that the patient can initially customize the tooth accepting faces by heating the dental blocks, biting into the tooth accepting faces, and then allowing the dental blocks to cool, producing tooth accepting faces that are customized to the shape of the user's teeth (usually the user's back molars).

In some embodiments, the adjustment further comprises configuring the pivoting dental blocks (110) and said gaps to exert opposite spring-action forces on said upper and lower tooth-accepting faces (132u, 132l). This is often done by selecting the configurations and materials used in various springs and spring-like components associated with the pivoting dental blocks, as will be discussed shortly.

These spring-action forces are selected to be greater than the minimum amount needed to by the user to partially open their jaws (102, 104), but less than the maximum amount needed by the user to close said jaws against said spring-action forces. It is anticipated that these will differ between users, and some experimentation and adjustment will be required to customize the device for each user.

These adjustments will typically further comprise adjusting the lip opening fixture (154), so that when the user's face is in a relaxed resting state, the spring-action forces acting on the lip opening fixture and the lip opening fixture (154) itself enable the user to breathe through their mouth. However, when the user activates their jaw muscles or lip muscles to close their mouth, the user's jaw muscles and lip muscles should be able to easily overcome the opening spring-action forces on both the jaws and lip opening fixture. The idea is to enable the user, while asleep, to close their lips and/or swallow saliva without conscious effort. Thus, the user can generally breathe through their mouth, while at the same time avoiding a dry mouth and/or drooling.

Figure 2:
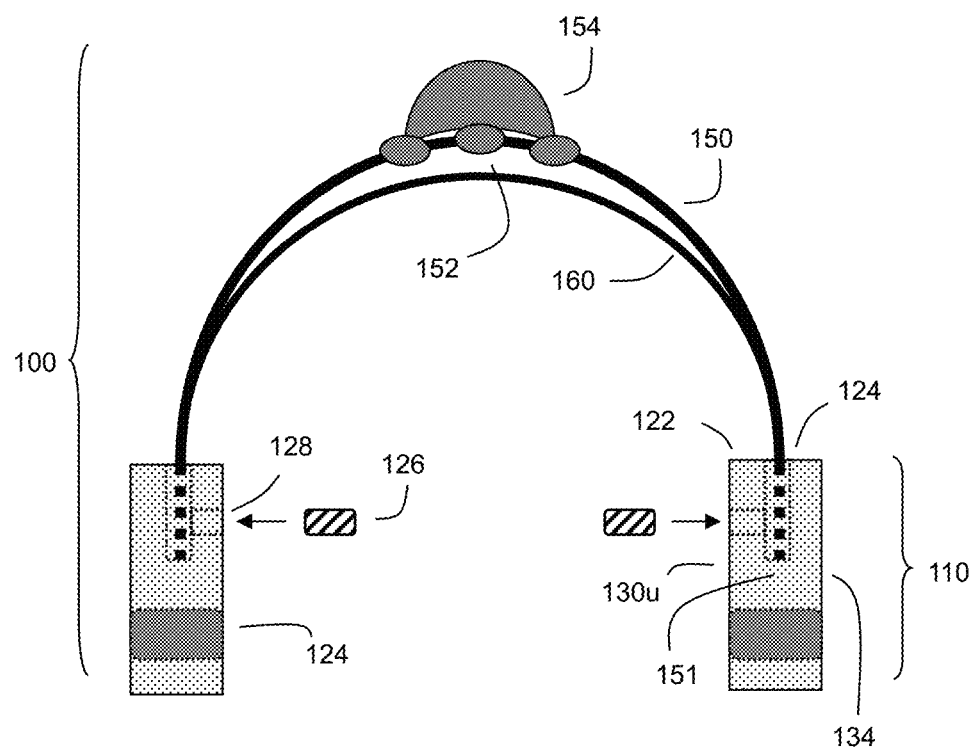
FIG. 2 shows an overhead view of the mouthpiece device.

FIG. 2 shows an overhead view of the mouthpiece device (100). This shows a top view of the dental blocks (110), as well as the upper (150) and lower (160) archwires. A lip-opening fixture (154) is attached to the upper archwire (150). The archwires fit inside wire holes (124) in the wire interface faces (here only the upper faces 122u are shown), and can be held in place by screws (126) inserted into screw holes (128) in the upper and lower fastener faces (130u, 130l, here only 130u is shown). In some embodiments, spring-action tension devices may be placed along the outside (cheek side) of the dental blocks (110), in which case these cheek-side faces are designated "tension-mount faces" (134u, and 134l). Here again, as before, (134u) would be the tension mount face on the upper portion of the dental block (110), while (134l) would be the tension mount face on the lower portion of the dental block.

Adjustments for Growing Jaws During Childhood:

Children's jaws grow during childhood, and a device initially configured to fit the dimensions of a younger child's jaw may fit less well as the child ages and the child's jaw grows. Although large changes in jaw size, or the growth of new back molars, may require that the device be refitted, smaller changes can often be accomplished by, for example, loosening screws (126), pulling the ends of the archwires closer towards the edge of the wire holes (124), and then tightening screws (126). In some embodiments, to make small changes to the shape of the arch, additional holes and screws may be placed in the dental blocks to apply side forces to the archwires, thus resulting in minor changes in archwire shape. In still other embodiments, additional fixtures may be placed near the center or archwire, such as at or near the lip-opening fixture (154), which can apply or relax tension on the archwire, thus also effecting minor alterations in the archwire's shape.

Figure 3:
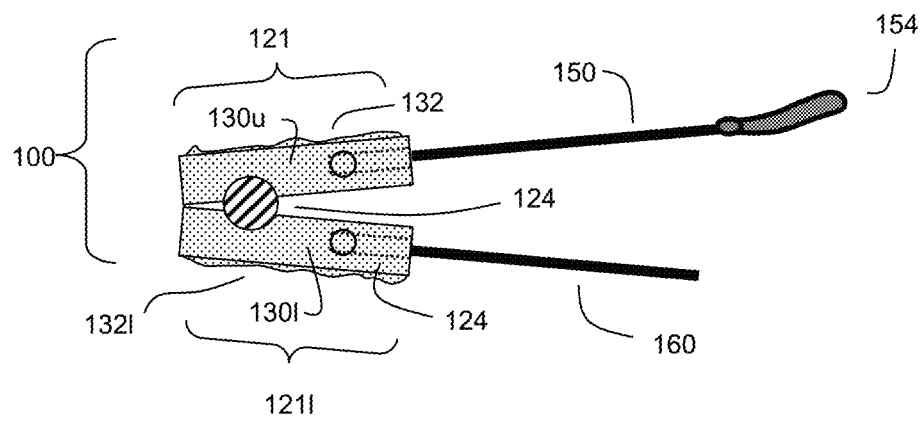
FIG. 3 shows a side view of the mouthpiece device, here seen from a bisected view from inside the user's jaw.

FIG. 3 shows a side view of the mouthpiece device (100), here seen from a bisected view as if from inside the user's jaw. This enables the upper and lower fastener faces (130u, 130l) to be more easily seen.

In this embodiment, the pivoting dental blocks (110) are each divided into an upper portion (121u) and a lower portion (121l), and the two portions are connected by a mechanical pivot (124). The upper portion has a tooth-accepting face (132u) that has recesses that can accommodate the user's upper molars or other teeth. The lower portion also has a tooth-accepting face (132l) with recesses that can accommodate the user's lower molars or other teeth. A lip-opening fixture (154) is attached to the upper archwire (150), but (in this example) not to the lower archwire (160). The dotted lines show the approximate locations of the wire holes (124) inside the dental blocks.

Put alternatively, in some embodiments, the pivoting dental blocks (110) comprise an upper portion (121u) and a lower portion (121l). In this embodiment, these portions are connected by a mechanical pivot (124). The upper wire interface face (122u), upper fastener face (130u), and the upper tooth accepting face (132u) are positioned on said upper portion (121*u*). By contrast, the lower wire interface face (121*l*), lower fastener face (130*l*), and lower tooth accepting face (132*l*) are positioned on the lower portion (121*l*).

In some embodiments, the mechanical pivot can comprise a spring, which serves both as a pivot and to provide at least some of the jaw-opening spring forces. In other embodiments, the mechanical pivot (124) can comprise a ball joint. Here the jaw opening spring forces may be provided by alternative types of spring devices, to be discussed shortly.

Figure 4:
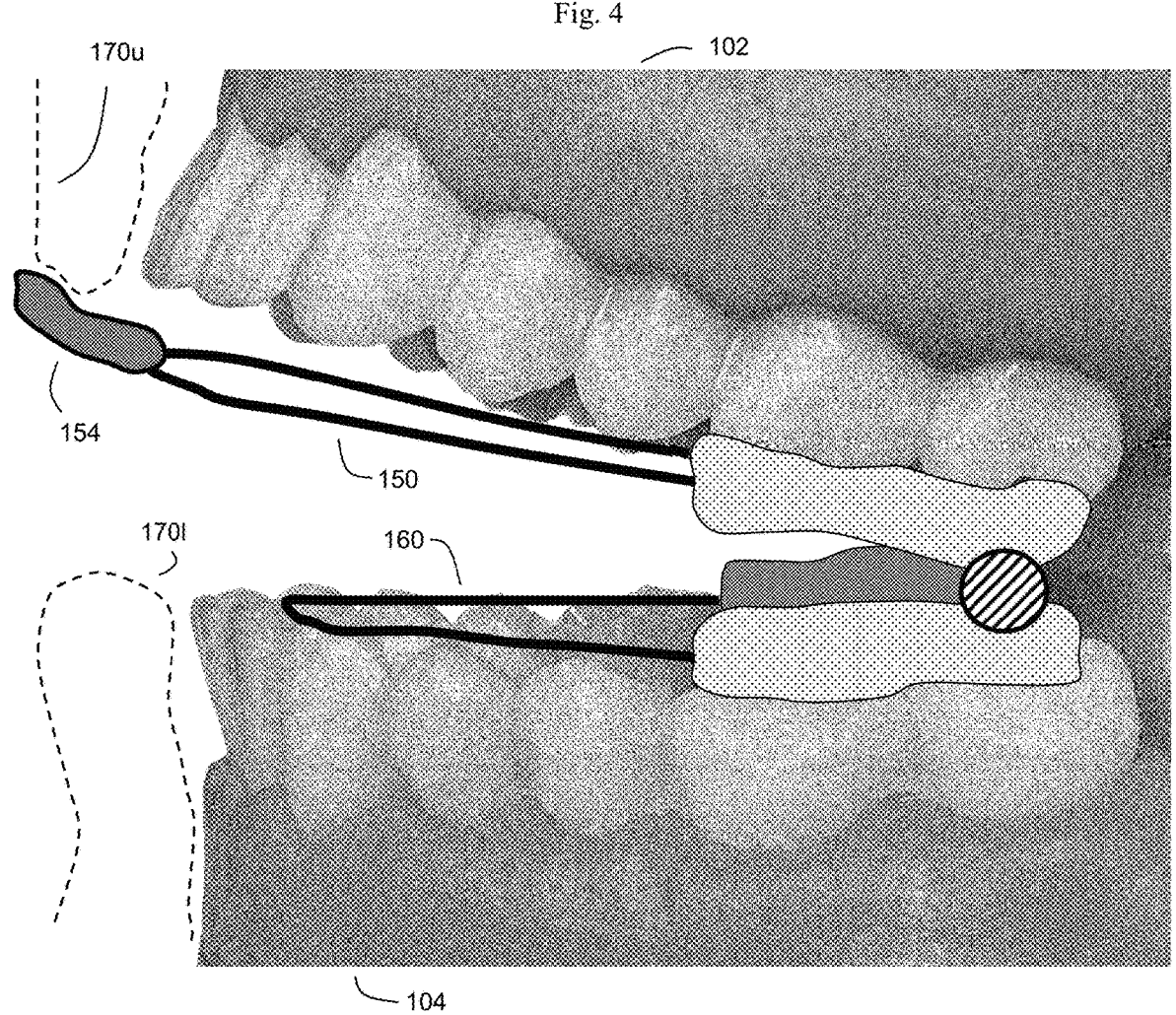
FIG. 4 shows a side view of how the mouthpiece device can fit between the upper and lower jaws of a human user and apply a gentle force to open both the user's jaws and the user's lips.

FIG. 4 shows a side view of how the mouthpiece device (100) can fit between the upper (102) and lower (104) jaws of a human user and apply a gentle force to open both the user's jaws and the user's lips (170*u*, 170*l*). Here the approximate outline of the human user's upper and lower lips (170*u*, 170*l*) is shown in dashed lines. As previously discussed, the lip-opener fixture (154) is configured so that when the device is inserted in the user's mouth, the lip-opener fixture can protrude slightly (usually ¼ inch to ½ inch) between the user's lips (170*u*, 170*l*) and apply a gentle opening pressure to at least the user's upper lip (170*u*) when the user's lips are relaxed.

In this disclosure, "gentle force" means enough force to open the jaws or lips when the jaw or lip muscles are relaxed but not enough force to open the jaw or lips when the jaw or lip muscles are working to close the jaws or lips.

To support the lip opening fixture, in some embodiments, at least the upper archwire (150) may further comprise at least one upper attachment device (152) disposed midway between the opposite sides or ends (151) of the archwire. The lip opening fixture (154) often comprises at least one upper lip opening fixture configured to attach to this at least one upper attachment device (152). However other embodiments are possible.

Figure 5:
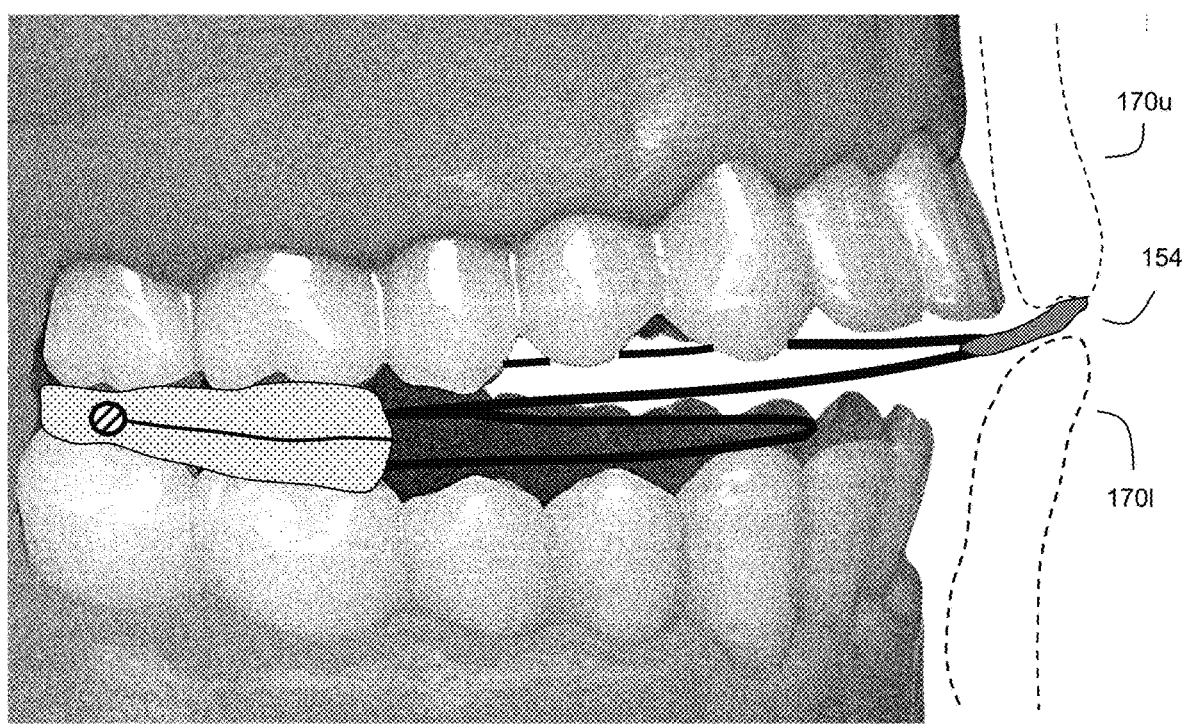
FIG. 5 shows a side view of how the device's mouth opening force can also be selected to enable the human user to easily close their jaws to swallow when desired.

FIG. 5 shows a side view of how the device's mouth opening force can also be selected to enable the human user to easily close their jaws to swallow when desired. Similarly, the lip opening fixture (154) can be configured so that the human user can also easily close their lips to swallow. The jaw opening force can be adjusted by selecting suitable springs on the pivoting dental blocks. This lip opening force adjustment can be done by selecting the stiffness and spring action of the archwires (150) and the lip-opener fixture (154).

Figure 6:
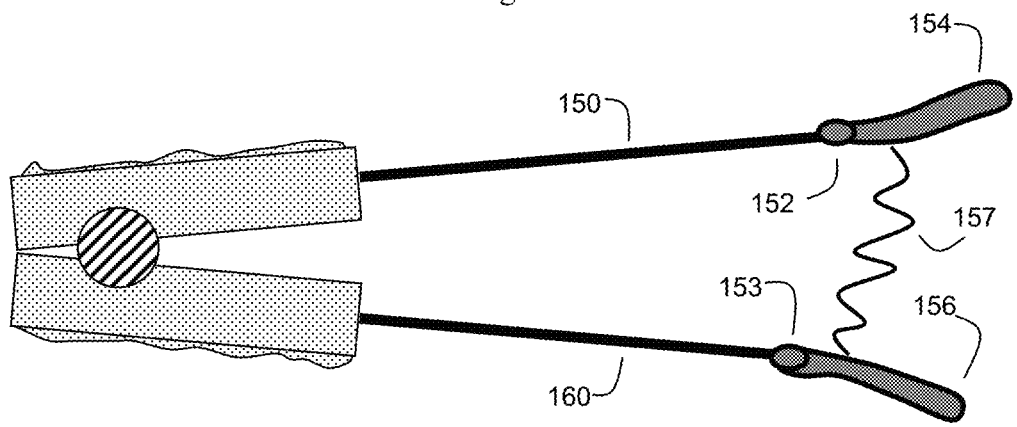
FIG. 6 shows a side view of the device, showing that in some embodiments, both the upper and lower archwires may be equipped with lip-opening fixtures.

FIG. 6 shows a side view of the device, showing that in alternative embodiments, both the upper (150) and lower archwires (160) may be equipped with lip-opening fixtures (154, 156).

Note that the lower archwire (160) itself can comprise a lower attachment device (153) disposed midway between the archwire's opposite sides or ends (151). In this embodiment, the lip opening fixture comprises at least one lower lip opening fixture (156) configured to attach to at least one lower attachment device (153).

In embodiments, when there are two lip opening fixtures, the upper lip opening fixture and the lower lip opening fixture may further comprise (and be connected by) a lip opening spring (157) configured to separate the user's lips while these lips are relaxed.

Figure 7:
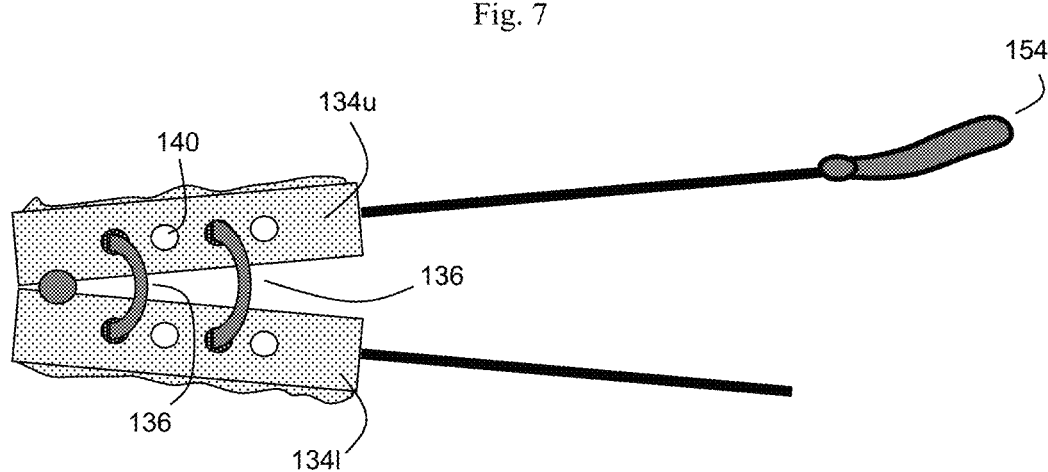
FIG. 7 shows an alternate side view of the device, showing how at least one deformable spring-like material can be mounted on various positions along a series of tension mount holes.

FIG. 7 shows an alternate side view of the device, showing how at least one deformable spring-like material (here, two materials 136*a* and 136*b* are shown) can be mounted on various positions along a series of tension mount holes (140) positioned on the device's upper and lower tension mount faces (134*u*, 134*l*). This also allows the spring-action forces to be adjusted for a given user. These materials can, for example, be elastic materials selected with a tendency to transition from a curved shape to a more linear shape with the desired amount of force.

Figure 8:
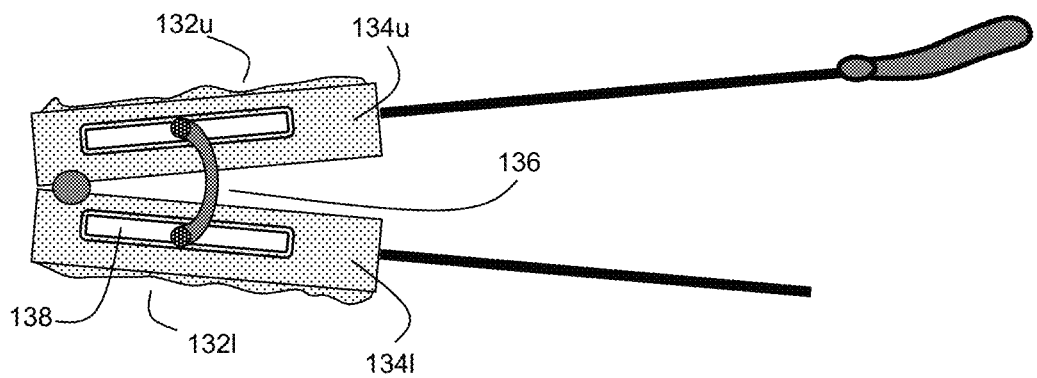
FIG. 8 shows an alternate side view of the device, showing how at least one deformable spring-like material can be mounted on various positions along a slot on the device's upper and lower tension mount faces.

FIG. 8 shows an alternate side view of the device, showing how at least one deformable spring-like material (136*a*) can be mounted on various positions along a slot (138) on the device's upper and lower tension mount faces (134*u*, 134*l*). This also allows the spring-action forces to be adjusted for a given user.

In some embodiments, the pivoting dental blocks (110) may further comprise gap-separated upper and lower tension mount faces (134*u*, 134*l*). These upper and lower tension mount faces are typically disposed both parallel to the gap-separated upper and lower fastener faces (130*u*, 130*l*) and also perpendicular to the upper and lower tooth-accepting faces (132*u*, 132*l*).

These upper and lower tension mount faces (134*u*, 134*l*) are termed this because they are the faces where various optional spring like materials may be mounted. Often this face is chosen as to avoid irritating the user's tongue, which will be on the opposite side of the dental block.

These upper and lower tension mount faces will typically further comprise any of a slot (138) or a plurality of mounting holes (140). This slot or plurality of mounting holes is configured to accept at least one deformable spring-like material (136*a*, 136*b*). This spring-like material is selected or configured so that, when disposed between the slots or mounting holes (and often affixed by screws), it exerts the appropriate amount of spring-force directed to cause the gap to widen (often against the opposing force of the user's jaw when the jaw muscles are relaxed).

Examples of suitable spring-like materials include deformable nickel-aluminum (nitinol) wires, elastomers, synthetic rubber, silicone, and the like.

Remember that there are two dental bocks (110). Thus often, the at least one deformable spring-like material comprises two deformable spring-like materials, one for each block, so that each material is connected to one of the pivoting dental blocks.

In some embodiments, however, employing more than one deformable spring-like material per dental block may be useful. Thus, in these embodiments, the at least one deformable spring-like material may comprise more than two deformable spring-like materials. Here at least one of the pivoting dental blocks is connected to more than one of these deformable spring-like materials.

Alternative Configurations

Figure 9:
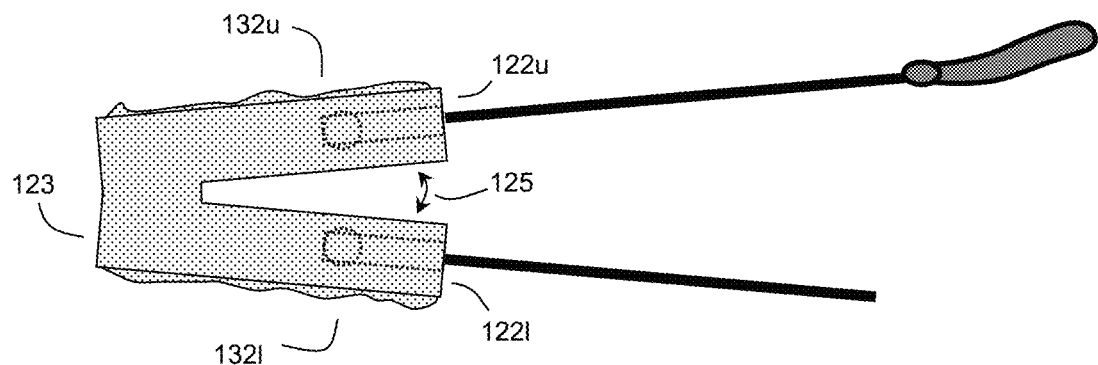
FIG. 9 shows that in some embodiments, the pivoting dental blocks can comprise a single portion of material partially bisected by a gap that divides the block into an upper portion and a lower portion on the wire-facing faces, with a single portion on the opposite face or side.

In some embodiments, the main portion of the dental block may be comprised of a material selected for elasticity to generate adequate spring-like forces. Such elastic materials can comprise Nylon (e.g. a $(C_{12}H_{22}N_2O_2)_n$ polymer, such as a hexanedioic acid, 1,6-diaminohexane polymer often referred to as Nylon-6,6). FIG. 9 shows that in some embodiments, the pivoting dental blocks (110) can comprise a single portion of a block material partially bisected by a gap (125) that divides the block into an upper portion and a lower portion on the wire-facing faces (sides 122*u*, 122*l*), with a single portion on the opposite face or side (123).

In these embodiments, the pivoting dental blocks (110) can comprise a single portion of block material partially bisected by a gap (125) that divides the dental block into an upper portion (122*u*) and a lower portion (122*l*) on the front wire-facing side, but only a single portion (123) on an opposite side. In this embodiment, the upper wire interface face (122*u*), upper fastener face (130*u*), and upper tooth accepting face (132*u*) are positioned on the upper portion. By contrast, the lower wire interface face (122*l*), lower fastener face (130*l*), and lower tooth accepting face (132*l*)

are positioned on the lower portion. In this embodiment, the pivoting dental blocks comprise an elastic material selected to be capable of repeatedly pivoting about said single portion (123).

Other Lip-Elevating Fixture Embodiments

Figure 10:
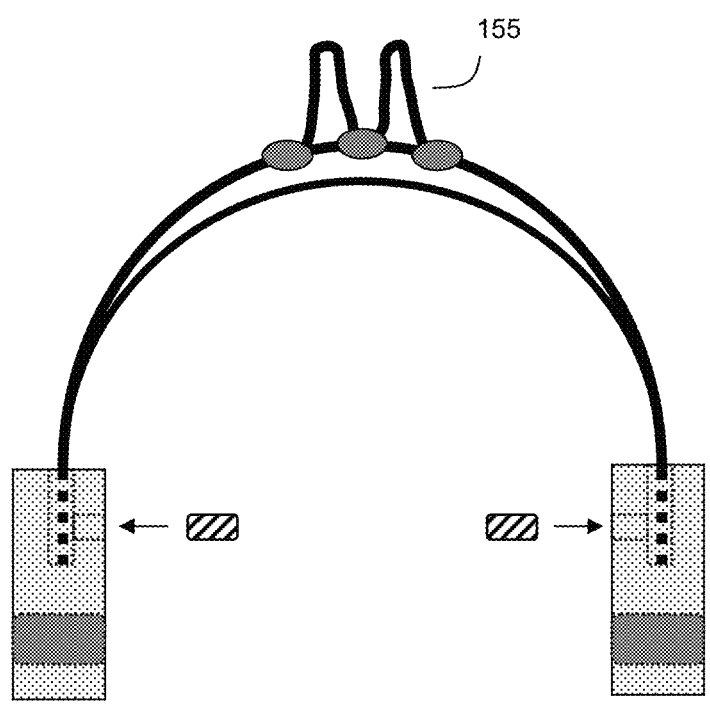
FIG. 10 shows that in some embodiments, the lip-elevating fixture can comprise at least one archwire fold configured to protrude between the middle of the user's lips.

FIG. 10 shows that in some embodiments, the lip-elevating fixture (154) can comprise at least one archwire fold (155) configured to protrude between the middle of the user's lips.

In this embodiment, the lip opening fixture comprises at least one archwire fold. This archwire fold is configured to protrude out of the middle of the user's mouth, and may also be further bent at an upward angle to elevate at least the middle of the lips when the lips are in a resting configuration.

Although for simplicity, only a single archwire has been shown for the upper and lower archwires (150, 160), this need not be limiting. In some configurations, to achieve the proper combination of strength and flexibility/rigidity, any of the upper and lower archwires may comprise a plurality of archwires.

About Adjusting the Device

As previously discussed, human users will vary in both jaw and mouth dimensions, as well as in jaw and lip muscle muscular strength and flexibility.

In terms of adjusting the size and shape of the device, in some embodiments, each of the gap-separated upper (130*u*) and lower (130*l*) fastener faces can comprise screw holes (128). These are aligned perpendicular to the wire holes (124) and in contact with these wire holes. These screw holes are configured so that a screw (126) inserted into the screw hole can be used to fasten the archwire wire ends (151) to the pivoting dental blocks (110). This allows for some adjustment.

For example, this adjustment can further comprise altering any of a length of said upper (150) or lower (160) archwire, or altering the distance of which any of said upper or lower archwire wire ends (151) enter any of the wire holes (124). Further, as previously described, the upper (132*u*) and lower (132*l*) tooth accepting faces can be adjusted (e.g., using thermoplastic material, and instructing the patient to bite into the thermoplastic material when it is hot) so that the adjustable mouthpiece device fits comfortably into the user's mouth.

Adjusting the Spring Forces:

Often, spring forces may be adjusted by providing a series of different spring pivots or spring-like materials and selecting those best suited to a given user. As a general guideline, the previously discussed work of Takai and Brunton suggest that the spring pivots or spring-like materials should be selected to provide a minimum amount of force greater than 4 Newtons of force and a maximum amount of force of less than 25 Newtons of force.

The invention claimed is:

1. A method of using an adjustable mouthpiece device configured to fit into mouth of a user and to facilitate breathing therefor said method comprising:
adjusting said adjustable mouthpiece device to fit onto jaws of the user, said adjustable mouthpiece device comprising:
two pivoting dental blocks, each configured to fit inside opposite sides of said jaw, said two pivoting dental blocks connected to each other by an upper archwire and a lower archwire, each archwire comprising wire ends;
each of said upper and lower archwires having between 170-190 degrees of curvature so that both wire ends adapted to fit inside said mouth;
each of the two pivoting dental blocks comprising gap-separated upper wire interface face and gap-separated lower wire interface face, gap-separated upper fastener face and gap-separated lower fastener face, upper tooth-accepting face and lower tooth-accepting face, thus creating a gap that separates at least said upper and lower wire interface faces;
each of said gap-separated upper and lower wire interface faces comprising a wire hole configured to admit one of said wire ends;
wherein when said wire ends are inserted into said wire holes, and fastened to said upper and lower wire interface faces, said upper archwire connects said upper wire interface faces of said two pivoting dental blocks, and said lower archwire connects said lower wire interface faces of said two pivoting dental blocks;
at least said upper archwire further configured with a lip opening fixture, positioned midway between said wire ends, which is configured to extend outside of said jaw and past at least a middle portion of said lip, so that said lip is partially elevated above normal resting state;
wherein said upper and lower tooth-accepting faces further comprise recesses configured to accommodate the user's teeth;
said adjusting further comprises configuring said two pivoting dental blocks and said gaps to exert opposite spring-action forces on said upper and lower tooth-accepting faces;
said spring-action forces selected to be greater than the minimum amount needed to partially open said jaws, but less than the maximum amount needed to close said jaws against said spring-action forces; and
wherein said adjusting further comprise adjusting said lip opening fixture, so that when said user's face is in said normal resting state, said spring-action forces and said lip opening fixture enable said user to breathe through said mouth, and when said user activates jaw muscles or lip muscles, said jaw muscles and lip muscles can overcome said spring-action forces and said lip opening fixture, thus enabling said user, during sleeping state, to close the lips and/or to swallow the saliva.

2. The method of claim 1, wherein said two pivoting dental blocks comprise an upper portion and a lower portion, said portions connected by a mechanical pivot;
wherein said gap-separated upper wire interface face, gap-separated upper fastener face, and gap-separated upper tooth-accepting face are positioned on said upper portion, and said gap-separated lower wire interface face, gap-separated lower fastener face, and gap-separated lower tooth-accepting face are positioned on said lower portion.

3. The method of claim 2, wherein said mechanical pivot comprises a ball joint.

4. The method of claim 1, wherein at least said upper archwire comprises an upper attachment device disposed midway between said opposite sides, and said lip opening fixture comprises at least one upper lip opening fixture configured to attach to at least one upper attachment device.

5. The method of claim 4, wherein said lower archwire comprises a lower attachment device disposed midway between said opposite sides, and said lip opening fixture comprises at least one lower lip opening fixture configured to attach to at least one lower attachment device.

6. The method of claim 4, wherein at least one of said upper lip opening fixture and said lower lip opening fixture further contain a lip opening spring configured to separate said user's lips while said lips are relaxed.

7. The method of claim 1, wherein said two pivoting dental blocks further comprise gap-separated upper tension mount face and gap-separated lower tension mount face, said gap-separated upper and lower tension mount faces disposed parallel to said gap-separated upper and lower fastener faces, and perpendicular to said upper and lower tooth-accepting faces;

said gap-separated upper and lower tension mount faces each further comprising any one of a slot or a plurality of mounting holes, said slot or plurality of mounting holes configured to accept at least one deformable spring-like material, wherein the at least one deformable spring-like material is configured to exert spring-force directed to cause said gap to widen.

8. The method of claim 7, wherein said at least one deformable spring-like material comprises two deformable spring-like materials, each of the two deformable spring-like material is connected to one of said two pivoting dental blocks.

9. The method of claim 7, wherein said at least one deformable spring-like material comprises more than two deformable spring-like materials, and wherein at least one of said two pivoting dental blocks is connected to more than one said deformable spring-like materials.

10. The method of claim 1, wherein said two pivoting dental blocks comprise a single portion of a block material partially bisected by a gap that divides said dental block into an upper portion and a lower portion on a front wire-facing side, and a single portion on an opposite side;

wherein said gap-separated upper wire interface face, said gap-separated upper fastener face, and upper tooth-accepting face are positioned on said upper portion, and said gap-separated lower wire interface face, gap-separated lower fastener face, and lower tooth-accepting face are positioned on said lower portion;

said two pivoting dental blocks comprising an elastic block material selected to be capable of repeatedly pivoting about said single portion.

11. The method of claim 1, wherein said lip opening fixture comprises at least one archwire fold, said at least one archwire fold configured to protrude out of the middle of said mouth, and further bent at an upward angle so as to elevate at least the middle of said lips.

12. The method of claim 1, wherein any one of said upper and lower archwire comprise a plurality of archwires.

13. The method of claim 1, wherein each of said gap-separated upper and lower fastener faces comprises screw holes, each aligned perpendicular to said wire holes and in contact with said wire holes, and configured so that a screw inserted into said screw hole fastens said wire ends of said archwires to said two pivoting dental blocks; and said adjusting further comprising altering any one of a length of said upper or lower archwire, altering a distance of which any of said upper or lower archwire wire end enters any of said wire holes, and adjusting said upper and lower tooth-accepting faces so that said adjustable mouthpiece device fits into said mouth.

14. The method of claim 1, wherein said minimum amount of said spring-action force is greater than 4 Newtons of force, and said maximum amount of said spring-action force is less than 25 Newtons of force.

15. The method of claim 1, further adjusting the middle portions of any of said archwires to improve the fit between said adjustable mouthpiece device and said mouth.

16. An adjustable mouthpiece device configured to fit into mouth of a user and to facilitate breathing therefor said method comprising:

adjusting said adjustable mouthpiece device to fit onto jaws of the user, said adjustable mouthpiece device comprising:

two pivoting dental blocks, each configured to fit inside opposite sides of said jaw, said two pivoting dental blocks connected to each other by an upper archwire and a lower archwire, each archwire comprising wire ends;

each of said upper and lower archwires having between 170-190 degrees of curvature so that both wire ends adapted to fit inside said mouth;

each of the two pivoting dental blocks comprising gap-separated upper wire interface face and gap-separated lower wire interface face, gap-separated upper fastener face and gap-separated lower fastener face, upper tooth-accepting face and lower tooth-accepting face, thus creating a gap that separates at least said upper and lower wire interface faces;

each of said gap-separated upper and lower wire interface faces comprising a wire hole configured to admit one of said wire ends;

wherein when said wire ends are inserted into said wire holes, and fastened to said upper and lower wire interface faces, said upper archwire connects said upper wire interface faces of said two pivoting dental blocks, and said lower archwire connects said lower wire interface faces of said two pivoting dental blocks;

at least said upper archwire further configured with a lip opening fixture, positioned midway between said wire ends, which is configured to extend outside of said jaw and past at least a middle portion of said lip, so that said lip is partially elevated above normal resting state;

wherein said upper and lower tooth-accepting faces further comprise recesses configured to accommodate the user's teeth;

said two pivoting dental blocks and said gaps to exert opposite spring-action forces on said upper and lower tooth-accepting faces;

said spring-action forces selected to be greater than the minimum amount needed to partially open said jaws, but less than the maximum amount needed to close said jaws against said spring-action forces; and wherein said adjusting further comprise adjusting said lip opening fixture, so that when said user's face is in said normal resting state, said spring-action forces and said lip opening fixture enable said user to breathe through said mouth, and when said user activates jaw muscles or lip muscles, said jaw muscles and lip muscles can overcome said spring-action forces and said lip opening fixture, thus enabling said user, during sleeping state, to close the lips and/or to swallow the saliva.

17. The method of claim 16, wherein said two pivoting dental blocks comprise an upper portion and a lower portion, said portions connected by a mechanical pivot;

wherein said gap-separated upper wire interface face, gap-separated upper fastener face, and gap-separated upper tooth-accepting face are positioned on said upper portion, and said gap-separated lower wire interface face, gap-separated lower fastener face, and gap-separated lower tooth-accepting face are positioned on said lower portion.

18. The device claim 16, wherein at least said upper archwire comprises an upper attachment device disposed midway between said opposite sides, and said lip opening fixture comprises at least one upper lip opening fixture configured to attach to at least one upper attachment device; wherein said lower archwire comprises a lower attachment device disposed midway between said opposite sides, and said lip opening fixture comprises at least one lower lip opening fixture configured to attach to at least one lower attachment device; and wherein at least one of said upper lip opening fixture and said lower lip opening fixture further contain a lip opening spring configured to separate said user's lips while said lips are relaxed.

19. The device of claim 16, wherein said two pivoting dental blocks further comprise gap-separated upper tension mount face and gap-separated lower tension mount face, said gap-separated upper and lower tension mount faces disposed parallel to said gap-separated upper and lower fastener faces, and perpendicular to said upper and lower tooth-accepting faces;

said gap-separated upper and lower tension mount faces each further comprising any one of a slot or a plurality of mounting holes, said slot or plurality of mounting holes configured to accept at least one deformable spring-like material, wherein the at least one deformable spring-like material is configured to exert spring-force directed to cause said gap to widen;

wherein said at least one deformable spring-like material comprises two deformable spring-like materials, each of the two deformable spring-like material is connected to one of said two pivoting dental blocks; and wherein said at least one deformable spring-like material comprises more than two deformable spring-like materials, and wherein at least one of said two pivoting dental blocks is connected to more than one said deformable spring-like materials.

* * * * *